(12) United States Patent
Liebmann et al.

(10) Patent No.: US 8,288,512 B2
(45) Date of Patent: *Oct. 16, 2012

(54) USE OF AMPHIPHILIC SELF-ASSEMBLING PROTEINS FOR FORMULATING POORLY WATER-SOLUBLE EFFECT SUBSTANCES

(75) Inventors: Burghard Liebmann, Bensheim (DE); Marcus Fehr, Speyer (DE); Daniel Hümmerich, Frankenthal (DE); Ingrid Martin, Ludwigshafen (DE); Mario Brands, Ludwigshafen (DE); Arne Ptock, Neuss (DE); Thomas Scheibel, Bayreuth (DE)

(73) Assignee: BASF SE, Ludwigshafen (DE)

( * ) Notice: Subject to any disclaimer, the term of this patent is extended or adjusted under 35 U.S.C. 154(b) by 1014 days.

This patent is subject to a terminal disclaimer.

(21) Appl. No.: 12/161,364

(22) PCT Filed: Jan. 19, 2007

(86) PCT No.: PCT/EP2007/050541
§ 371 (c)(1),
(2), (4) Date: Aug. 7, 2008

(87) PCT Pub. No.: WO2007/082936
PCT Pub. Date: Jul. 26, 2007

(65) Prior Publication Data
US 2010/0278883 A1    Nov. 4, 2010

(30) Foreign Application Priority Data
Jan. 20, 2006    (EP) .................................... 06100671

(51) Int. Cl.
*C07K 1/00* (2006.01)
*A61K 9/00* (2006.01)
*A61K 38/16* (2006.01)
*A01N 25/00* (2006.01)

(52) U.S. Cl. ........ 530/350; 424/401; 424/405; 514/21.2

(58) Field of Classification Search ........................ None
See application file for complete search history.

(56) References Cited

U.S. PATENT DOCUMENTS

| | | |
|---|---|---|
| 7,105,176 B2 | 9/2006 | Auweter et al. |
| 2002/0110599 A1 * | 8/2002 | Auweter et al. ............. 424/499 |
| 2003/0185865 A1 | 10/2003 | Jentzsch et al. |
| 2004/0265260 A1 * | 12/2004 | Tsubouchi et al. ........ 424/70.14 |
| 2005/0118209 A1 | 6/2005 | Jentszch et al. |
| 2008/0125499 A1 | 5/2008 | Jensen et al. |

FOREIGN PATENT DOCUMENTS

| | | |
|---|---|---|
| DE | 10059213 A1 | 6/2002 |
| DE | 102004057587 A1 | 6/2006 |
| WO | WO-02/07698 A2 | 1/2002 |
| WO | WO-03/059312 A2 | 7/2003 |
| WO | WO2005123114 * | 6/2004 |
| WO | WO-2005/012000 A2 | 2/2005 |
| WO | WO-2005/123114 A2 | 12/2005 |
| WO | WO-2007/082923 A2 | 7/2007 |

OTHER PUBLICATIONS

Hill et al. "Amphiphile Nature of k-Casein as the Basis of its Micelle Stabilizin Property", Nature, 221, 1969, pp. 635.*
Winkler, S. and Kaplan, D.L., "Molecular biology of spider silk," Reviews in Molecular Biotechnology, 2000, vol. 74, pp. 85-93.
Hümmerich, D. et al., "Primary structure elements of spider dragline silks and their contribution to protein solubility," Biochemistry, 2004, vol. 43, pp. 13604-13612.
Guerette, P.A., et al., "Silk properties determined by gland-specific expression of a spider fibroin gene family," Science, 1996, vol. 272, pp. 112-115.
Craig, C., "Evolution of arthropod silks," Annu. Rev. Entomol, 1997, vol. 42, pp. 231-267.

* cited by examiner

Primary Examiner — Daniel Sullivan
Assistant Examiner — Melissa Javier
(74) Attorney, Agent, or Firm — Connolly Bove Lodge & Hutz, LLP (57) ABSTRACT

The invention relates to the use of amphiphilic self-assembling proteins for formulating poorly water-soluble effect substances.

3 Claims, 5 Drawing Sheets

SEQUENCE LISTING

```
<160> NUMBER OF SEQ ID NOS: 1

<210> SEQ ID NO 1
<211> LENGTH: 576
<212> TYPE: PRT
<213> ORGANISM: Artificial Sequence
<220> FEATURE:
<223> OTHER INFORMATION: Synthetic spider silk C16 protein

<400> SEQUENCE: 1

Met Ala Ser Met Thr Gly Gly Gln Gln Met Gly Arg Gly Ser Met Gly
1               5                   10                  15

Ser Ser Ala Ala Ala Ala Ala Ala Ala Ser Gly Pro Gly Gly Tyr
            20                  25                  30

Gly Pro Glu Asn Gln Gly Pro Ser Gly Pro Gly Gly Tyr Gly Pro Gly
            35                  40                  45

Gly Pro Gly Ser Ser Ala Ala Ala Ala Ala Ala Ala Ser Gly Pro
        50                  55                  60

Gly Gly Tyr Gly Pro Glu Asn Gln Gly Pro Ser Gly Pro Gly Gly Tyr
65                  70                  75                  80

Gly Pro Gly Gly Pro Gly Ser Ser Ala Ala Ala Ala Ala Ala Ala Ala
                85                  90                  95

Ser Gly Pro Gly Gly Tyr Gly Pro Glu Asn Gln Gly Pro Ser Gly Pro
                100                 105                 110

Gly Gly Tyr Gly Pro Gly Gly Pro Gly Ser Ser Ala Ala Ala Ala Ala
            115                 120                 125

Ala Ala Ala Ser Gly Pro Gly Gly Tyr Gly Pro Glu Asn Gln Gly Pro
    130                 135                 140

Ser Gly Pro Gly Gly Tyr Gly Pro Gly Gly Pro Gly Ser Ser Ala Ala
145                 150                 155                 160

Ala Ala Ala Ala Ala Ala Ser Gly Pro Gly Gly Tyr Gly Pro Glu Asn
                165                 170                 175

Gln Gly Pro Ser Gly Pro Gly Gly Tyr Gly Pro Gly Gly Pro Gly Ser
                180                 185                 190

Ser Ala Ala Ala Ala Ala Ala Ala Ser Gly Pro Gly Gly Tyr Gly
            195                 200                 205

Pro Glu Asn Gln Gly Pro Ser Gly Pro Gly Gly Tyr Gly Pro Gly Gly
            210                 215                 220
```

```
Pro Gly Ser Ser Ala Ala Ala Ala Ala Ala Ser Gly Pro Gly
225                 230                 235             240

Gly Tyr Gly Pro Glu Asn Gln Gly Pro Ser Gly Pro Gly Tyr Gly
            245                 250             255

Pro Gly Gly Pro Gly Ser Ser Ala Ala Ala Ala Ala Ala Ala Ser
        260             265                 270

Gly Pro Gly Gly Tyr Gly Pro Glu Asn Gln Gly Pro Ser Gly Pro Gly
    275             280                 285

Gly Tyr Gly Pro Gly Gly Pro Gly Ser Ser Ala Ala Ala Ala Ala
    290             295             300

Ala Ala Ser Gly Pro Gly Gly Tyr Gly Pro Glu Asn Gln Gly Pro Ser
305             310             315                 320

Gly Pro Gly Gly Tyr Gly Pro Gly Gly Pro Gly Ser Ser Ala Ala Ala
                325             330             335

Ala Ala Ala Ala Ala Ser Gly Pro Gly Gly Tyr Gly Pro Glu Asn Gln
            340             345             350

Gly Pro Ser Gly Pro Gly Gly Tyr Gly Pro Gly Gly Pro Gly Ser Ser
        355             360             365

Ala Ala Ala Ala Ala Ala Ala Ser Gly Pro Gly Gly Tyr Gly Pro
    370             375             380

Glu Asn Gln Gly Pro Ser Gly Pro Gly Gly Tyr Gly Pro Gly Gly Pro
385             390             395             400

Gly Ser Ser Ala Ala Ala Ala Ala Ala Ala Ser Gly Pro Gly Gly
            405             410             415

Tyr Gly Pro Glu Asn Gln Gly Pro Ser Gly Pro Gly Gly Tyr Gly Pro
            420             425             430

Gly Gly Pro Gly Ser Ser Ala Ala Ala Ala Ala Ala Ala Ser Gly
        435             440             445

Pro Gly Gly Tyr Gly Pro Glu Asn Gln Gly Pro Ser Gly Pro Gly Gly
    450             455             460

Tyr Gly Pro Gly Gly Pro Gly Ser Ser Ala Ala Ala Ala Ala Ala
465             470             475             480

Ala Ser Gly Pro Gly Gly Tyr Gly Pro Glu Asn Gln Gly Pro Ser Gly
            485             490             495

Pro Gly Gly Tyr Gly Pro Gly Gly Pro Gly Ser Ser Ala Ala Ala Ala
        500             505             510

Ala Ala Ala Ala Ser Gly Pro Gly Gly Tyr Gly Pro Glu Asn Gln Gly
    515             520             525

Pro Ser Gly Pro Gly Gly Tyr Gly Pro Gly Gly Pro Gly Ser Ser Ala
530             535             540

Ala Ala Ala Ala Ala Ala Ser Gly Pro Gly Gly Tyr Gly Pro Glu
545             550             555             560

Asn Gln Gly Pro Ser Gly Pro Gly Gly Tyr Gly Pro Gly Gly Pro Gly
            565             570             575
```

USE OF AMPHIPHILIC SELF-ASSEMBLING PROTEINS FOR FORMULATING POORLY WATER-SOLUBLE EFFECT SUBSTANCES

RELATED APPLICATIONS

This application is a national stage application under 35 U.S.C. §371 of PCT/EP2007/050541, filed Jan. 19, 2007, which is incorporated by reference in its entirety, and claims priority of European application 06100671.4, filed Jan. 20, 2006, which is incorporated by reference in its entirety.

SEQUENCE LISTING SUBMISSION

The Sequence Listing associated with this application is filed in electronic format via EFS-Web and hereby incorporated by reference in its entirety into the specification. The name of the text file containing the Sequence Listing is SequenceList_12810_00727_US. The size of the text file is 5.39 KB, and the text file was created on Jul. 9, 2008.

The present invention relates to the use of amphiphilic self-assembling proteins for formulating poorly water-soluble effect substances.

Prior Art

DE 10059213A1 describes a method of producing solid preparations of water-insoluble or poorly water-soluble active substances by dispersing the active substances in a protein-containing protective colloid, flocculation and separating off the active substance coated with the protective colloid and conversion to a dry powder. Casein and bovine gelatin, porcine gelatin and fish gelatin are specified as preferred protective colloids.

DE 102004057587A1 describes aqueous dispersions of a mixture of poorly water-soluble active substances and protein material from single-celled organisms and dry powders produced therefrom.

Objective

The methods of formulating water-insoluble or poorly water-soluble active substances and effect substances known to date do not satisfy all of the requirements which are placed on an active substance formulated in particular for cosmetic and pharmaceutical use, such as thermal stability, oxidation stability and photostability, mechanical stability, toxic acceptability.

It was therefore the object to provide a method which permits the formulation of poorly water-soluble active substances and in so doing better satisfies the abovementioned criteria than the methods known from the prior art.

DESCRIPTION OF THE INVENTION

In a first embodiment, the present invention relates to the use of amphiphilic, self-assembling proteins for formulating poorly water-soluble effect substances.

Amphiphilic self-assembling proteins are suitable as formulation auxiliaries for poorly water-soluble hydrophobic active substances. As a result of their amphiphilic molecular character, these proteins are able to stabilize hydrophobic active substances in aqueous solutions. Their self-assembling properties allow these proteins to take on higher molecular weight structures and thus permanently encapsulate hydrophobic active substances.

The invention further provides a method of producing effect substance formulations, where
(i) the poorly water-soluble effect substance is mixed together with the amphiphilic self-assembling protein in a common disperse phase and
(ii) then a phase separation into a phase rich in protein and effect substance, and a phase low in protein and effect substance, is carried out.

The phase rich in protein and effect substance can subsequently be hardened and separated off as mechanically stable effect-substance-comprising protein microbeads and, if appropriate, dried.

(i) Amphiphilic Self-assembling Proteins

Amphiphilic self-assembling proteins consist of polypeptides which are composed of amino acids, in particular of the 20 naturally occurring amino acids. The amino acids may also be modified, for example acetylated, glycosylated, farnesylated.

Suitable amphiphilic self-assembling proteins for the formulation of poorly water-soluble effect substances are those proteins which can form protein microbeads. Protein microbeads have a globular configuration with an average particle diameter of from 0.1 to 100 μm, in particular from 0.5 to 20 μm, preferably from 1 to 5 μm and particularly preferably from 2 to 4 μm.

Protein microbeads can preferably be produced by the method described below:

The protein is dissolved in a first solvent. Solvents that can be used here are, for example, aqueous salt solutions. In particular, highly concentrated salt solutions with a concentration greater than 2, in particular greater than 4 and particularly preferably greater than 5 molar, whose ions have more marked chaotropic properties than sodium ions and chloride ions are suitable. One example of such a salt solution is 6 M guanidinium thiocyanate or 9 M lithium bromide. Furthermore, organic solvents can be used to dissolve the proteins. In particular, fluorinated alcohols or cyclic hydrocarbons or organic acids are suitable. Examples thereof are hexafluoroisopropanol, cyclohexane and formic acid. The production of the protein microbeads can take place in the described solvents. Alternatively, this solvent can be replaced by a further solvent, e.g. low-concentration salt solutions (c<0.5 M) through dialysis or dilution. The final concentration of the dissolved protein should be between 0.1-100 mg/ml. The temperature at which the method is carried out is usually 0-80° C., preferably 5-50° C. and particularly preferably 10-40° C.

When using aqueous solutions, these can also be admixed with a buffer, preferably in the pH range 4-10, particularly preferably 5-9, very particularly preferably 6-8.5.

By adding an additive, phase separation is induced. Here, a protein-rich phase emulsified in the mixture of solvent and additive is formed. On account of surface effects, emulsified protein-rich droplets assume a round shape. Through the choice of solvent, of additive and of protein concentration, the average diameter of the protein microbeads can be adjusted to values between 0.1 μm and 100 μm.

Additives which can be used are all substances which, on the one hand, are miscible with the first solvent and, on the other hand, induce the formation of a protein-rich phase. If microbead formation is carried out in organic solvents, suitable organic substances for this purpose have a lower polarity than the solvent, e.g. toluene. In aqueous solutions, salts whose ions have more marked cosmotropic properties than sodium ions and chloride ions (e.g. ammonium sulfate; potassium phosphate) can be used as additive. The final concentration of the additive should be between 1% and 50% by weight, based on the protein solution, depending on the nature of the additive.

The protein-rich droplets are fixed by hardening, with the round shape being retained. Fixing is based here on the development of strong intermolecular interactions. The type of interactions may be non-covalent, e.g. as a result of formation of intermolecular β-folding leaf crystals, or covalent, e.g. as a result of chemical crosslinking. Hardening can take place as a result of the additive and/or as a result of the addition of a further suitable substance. The hardening takes place at temperatures between 0 and 80° C., preferably between 5 and 60° C.

This further substance may be a chemical crosslinker. Here, a chemical crosslinker is understood as meaning a molecule in which at least two chemically reactive groups are joined together via a linker. Examples thereof are sulfhydryl-reactive groups (e.g. maleimides, pyridyl disulfides, α-haloacetyls, vinyl sulfones, sulfatoalkyl sulfones (preferably sulfatoethyl sulfones)), amine-reactive groups (e.g. succinimidyl esters, carbodiimides, hydroxymethylphosphine, imido esters, PFP esters, aldehydes, isothiocyanates etc.), carboxy-reactive groups (e.g. amines etc.), hydroxyl-reactive groups (e.g. isocyanates etc.), unselective groups (e.g. aryl azides etc.) and photoactivatable groups (e.g. perfluorophenyl azide etc.). These reactive groups can form covalent linkages with amine, thiol, carboxyl or hydroxyl groups present in proteins.

The stabilized microbeads are washed with a suitable further solvent, e.g. water, and then dried by methods known to the person skilled in the art, e.g. by lyophilization, contact drying or spray drying. The success of bead formation is checked using scanning electron microscopy.

Of suitability for producing protein microbeads are proteins which are present predominantly in intrinsically unfolded form in aqueous solution. This state can be calculated, for example, according to an algorithm, which forms the basis of the IUpred program (http://iupred.enzim.hu/index.html; The Pairwise Energy Content Estimated from Amino Acid Composition Discriminates between Folded and Intrinsically Unstructured Proteins; Zsuzsanna Dosztányi, Veronika Csizmók, Péter Tompa and István Simon; J. Mol. Biol. (2005) 347, 827-839). A predominantly intrinsically unfolded state is assumed when a value >0.5 is calculated according to this algorithm for more than 50% of the amino acid residues (prediction type: long disorder).

Further suitable proteins for formulating poorly water-soluble effect substances are silk proteins. In the text below, these are understood as meaning those proteins which comprise highly repetitive amino acid sequences and are stored in a liquid form in the animal and upon whose secretion, fibers form as a result of shearing or spinning (Craig, C. L. (1997) Evolution of arthropod silks. Annu. Rev. Entomol. 42: 231-67).

Particularly suitable proteins for formulating poorly water-soluble effect substances are spider silk proteins which were able to be isolated in their original form from spiders. Very particularly suitable proteins are silk proteins which were able to be isolated from the "Major Ampullate" gland of spiders.

Preferred silk proteins are ADF3 and ADF4 from the "Major Ampullate" gland of Araneus diadematus (Guerette et al., Science 272, 5258:112-5 (1996)).

Likewise suitable proteins for formulating poorly water-soluble effect substances are natural or synthetic proteins which are derived from natural silk proteins and which have been produced heterologously in prokaryotic or eukaryotic expression systems using genetic engineering methods. Non-limiting examples of prokaryotic expression organisms are *Escherichia coli, Bacillus subtilis, Bacillus megaterium, Corynebacterium glutamicum* etc. Nonlimiting examples of eukaryotic expression organisms are yeasts, such as *Saccharomyces cerevisiae, Pichia pastoris* etc., filamentous fungi, such as *Aspergillus niger, Aspergillus oryzae, Aspergillus nidulans, Trichoderma reesei, Acremonium chrysogenum* etc., mammalian cells, such as HeLa cells, COS cells, CHO cells etc., insect cells, such as Sf9 cells, MEL cells, etc.

Of particular preference for formulating poorly water-soluble effect substances are synthetic proteins which are based on repeat units of natural silk proteins. Besides the synthetic repetitive silk protein sequences, these can additionally comprise one or more natural nonrepetititive silk protein sequences (Winkler and Kaplan, J Biotechnol 74:85-93 (2000)).

Among the synthetic silk proteins, for formulating poorly water-soluble effect substances, preference is given to synthetic spider silk proteins which are based on repeated units of natural spider silk proteins. Besides the synthetic repetitive spider silk protein sequences, these can additionally comprise one or more natural nonrepetitive spider silk protein sequences.

Among the synthetic spider silk proteins, the so-called C16-protein is to be mentioned with preference (Huemmerich et al. Biochemistry, 43(42):13604-13612 (2004)). This protein has the polypeptide sequence shown in SEQ ID NO: 1. Besides the polypeptide sequence shown in SEQ ID NO:1, particularly functional equivalents, functional derivatives and salts of this sequence are also preferred.

According to the invention, "functional equivalents" are also to be understood in particular as meaning mutant which, in at least one sequence position of the abovementioned amino acid sequences, have an amino acid other than that specifically mentioned, but nevertheless have the property of packaging poorly water-soluble effect substances.

"Functional equivalents" thus comprise the mutants obtainable by one or more amino acid additions, substitutions, deletions and/or inversions, it being possible for said changes to occur in any sequence position provided they lead to a mutant with the profile of properties according to the invention. Functional equivalence is present in particular also when the reactivity pattern between mutants and unchanged polypeptide are in qualitative agreement.

In the above sense, "functional equivalents" are also "precursors" of the described polypeptides and also "functional derivatives" and "salts" of the polypeptides.

Here, "precursors" are natural or synthetic precursors of the polypeptides with or without the desired biological activity.

Examples of suitable amino acid substitutions are given in the table below:

| Original radical | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The expression "salts" is understood as meaning both salts of carboxyl groups and also acid addition salts of amino groups of the protein molecules according to the invention. Salts of carboxyl groups can be prepared in a manner known per se and comprise inorganic salts, such as, for example, sodium, calcium, ammonium, iron and zinc salts, and also salts with organic bases, such as, for example, amines, such as triethanolamine, arginine, lysine, piperidine and the like. Acid addition salts, such as, for example, salts with mineral acids, such as hydrochloric acid or sulfuric acid, and salts with organic acids, such as acetic acid and oxalic acid, are likewise provided by the invention.

"Functional derivatives" of polypeptides according to the invention can likewise be prepared on functional amino acid side groups or on their N— or C-terminal end with the help of known techniques. Derivatives of this type comprise, for example, aliphatic esters of carboxylic acid groups, amides of carboxylic acid groups, obtainable through reaction with ammonia or with a primary or secondary amine; N-acyl derivatives of free amino groups prepared by reaction with acyl groups; or O-acyl derivatives of free hydroxy groups prepared by reaction with acyl groups.

(ii) Poorly Water-soluble Effect Substances

In the text below, the terms poorly water-soluble effect substances and hydrophobic effect substances and hydrophobic active substances and effector molecules are used synonymously. In the text below, the term poorly water-soluble effect substances is used to refer to those compounds whose solubility in water at 20° C. is <5% by weight, preferably <1% by weight, particularly preferably <0.5% by weight, very particularly preferably <0.1% by weight.

Suitable poorly water-soluble effect substances are dyes, in particular those specified in the table below:

Particularly advantageous dyes are the oil-soluble or oil-dispersible compounds specified in the following list. The Colour Index Numbers (CIN) are given in the Rowe Colour Index, 3rd edition, Society of Dyers and Colourists, Bradford, England, 1971.

| Chemical or other name | CIN | Color |
| --- | --- | --- |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Ceres red; Sudan red; Fat red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfodiethylamide-1'-phenylazo)-3-hydroxy-5''-chloro-2'',4''-dimethoxy-2-naphthanilide | 12490 | red |
| Pigment Yellow 16 | 20040 | yellow |
| Pigment Yellow 13 | 21100 | yellow |
| Pigment Yellow 83 | 21108 | yellow |
| Solvent Yellow | 21230 | yellow |
| Food Yellow | 40800 | orange |
| trans-β-Apo-8'-carotenaldehyde (C30) | 40820 | orange |
| Ethyl trans-apo-8'-carotenoate (C30) | 40825 | orange |
| Canthaxanthin | 40850 | orange |
| Solvent Dye | 45396 | orange |
| Quinophthalone | 47000 | yellow |
| Pigment Violet 23 | 51319 | violet |
| 1,2-Dioxyanthraquinon, calcium-aluminum complex | 58000 | red |
| 1-Hydroxy-4-N-phenylaminoanthraquinone | 60724 | violet |
| 1-Hydroxy-4-(4'-methylphenylamino)anthraquinone | 60725 | violet |
| 1,4-Di(4'-methylphenylamino)anthraquinone | 61565 | green |
| N,N'-Dihydro-1,2,1',2'-anthraquinonazine | 69800 | blue |
| Vat Blue 6; Pigment Blue 64 | 69825 | blue |
| Vat Orange 7 | 71105 | orange |
| Indigo | 73000 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanines | 74260 | green |
| Bixin, Nor-Bixin | 75120 | orange |
| Lycopene | 75125 | yellow |
| trans-alpha-, beta- or gamma-carotene | 75130 | orange |
| Keto- and/or hydroxyl derivatives of carotene | 75135 | yellow |
| 1,7-Bis-(4-hydroxy-3-methoxyphenyl)1,6-heptadiene-3,5-dione | 75300 | yellow |

Further preferred effector molecules are fatty acids, in particular saturated fatty acids which carry an alkyl branch, particularly preferably branched eicosanoic acids, such as 18-methyleicosanoic acid.

Further preferred effector molecules are carotenoids. According to the invention, caroenoids are to be understood as meaning the following compounds and their esterified or glycosylated derivatives: β-carotene, lycopene, lutein, astaxanthin, zeaxanthin, cryptoxanthin, citranaxanthin, canthaxanthin, bixin, β-apo-4-carotenal, β-apo-8-carotenal, β-apo-8- carotenoate, neurosporene, echinenone, adonirubin, violaxanthin, torulene, torularhodin, individually or as a mixture. Preferably used carotenoids are β-carotene, lycopene, lutein, astaxanthin, zeaxanthin, citranaxanthin and canthaxanthin.

Further preferred effector molecules are vitamins, in particular retinoids and esters thereof.

Within the context of the present invention, retinoids means vitamin A alcohol (retinol) and its derivatives, such as vitamin A aldehyde (retinal), vitamin A acid (retinoic acid) and vitamin A ester (e.g. retinyl acetate, retinyl propionate and retinyl palmitate). The term retinoic acid here comprises both all-trans retinoic acid and also 13-cis retinoic acid. The terms retinal and retinal preferably comprise the all-trans compounds. A preferred retinoid used for the formulations according to the invention is all-trans retinol, referred to as retinol below.

Further preferred effector molecules are vitamins, provitamins and vitamin precursors from the groups A, C, E and F, in particular 3,4-didehydroretinol, β-carotene (provitamin of vitamin A), palmitic acid esters of ascorbic acid, tocopherols, in particular α-tocopherol and its esters, e.g. the acetate, the nicotinate, the phosphate and the succinate; also vitamin F, under which essential fatty acids, particularly linoleic acid, linolenic acid and arachidonic acid, are understood.

Further preferred effector molecules are lipophilic, oil-soluble antioxidants from the group vitamin E, i.e. tocopherol and derivatives thereof, gallic acid esters, flavonoids and carotenoids, and butylhydroxytoluene/anisole.

A further preferred effector molecule is lipoic acid and suitable derivatives (salts, esters, sugars, nucleotides, nucleosides, peptides and lipids).

Further preferred effector molecules are UV photoprotective filters. These are understood as meaning organic substances which are able to absorb ultraviolet rays and give off the absorbed energy again in the form of longer-wave radiation, e.g. heat.

Oil-soluble UV-B filters which can be used are, for example, the following substances:
3-benzylidenecamphor and derivatives thereof, e.g. 3-(4-methylbenzylidene)camphor;

4-aminobenzoic acid derivatives, preferably 2-ethylhexyl 4-(dimethylamino)benzoate, 2-octyl 4-(dimethylamino)benzoate and amyl 4-(dimethylamino)benzoate;
esters of cinnamic acid, preferably 2-ethylhexyl 4-methoxycinnamate, propyl 4-methoxycinnamate, isoamyl 4-methoxycinnamate, isopentyl 4-methoxycinnamate, 2-ethylhexyl 2-cyano-3-phenylcinnate (octocrylene);
esters of salicylic acid, preferably 2-ethylhexyl salicylate, 4-isopropylbenzyl salicylate, homomenthyl salicylate;
derivatives of benzophenone, preferably 2-hydroxy-4-methoxybenzophenone, 2-hydroxy-4-methoxy-4'-methylbenzophenone, hydroxy-4-methoxybenzophenone;
esters of benzalmalonic acid, preferably di-2-ethylhexyl 4-methoxybenzmalonate;
triazine derivatives, such as, for example, 2,4,6-trianilino-(p-carbo-2'-ethyl-1'-hexyloxy)-1,3,5-triazine (octyltriazone) and dioctylbutamidotriazone (Uvasorb® HEB);
propane-1,3-diones, such as, for example, 1-(4-tert-butylphenyl)-3-(4'-methoxyphenyl)propane-1,3-dione.

Particular preference is given to the use of esters of cinnamic acid, preferably 2-ethylhexyl 4-methoxycinnamate, isopentyl 4-methoxycinnamate, 2-ethylhexyl 2-cyano-3-phenylcinnamate (octocrylene).

Furthermore, the use of derivatives of benzophenone, in particular 2-hydroxy-4-methoxybenzophenone, 2-hydroxy-4-methoxy-4'-methylbenzophenone, 2,2'-dihydroxy-4-methoxybenzophenone, and the use of propane-1,3-diones, such as, for example, 1-(4-tert-butylphenyl)-3-(4'-methoxyphenyl)propane-1,3-dione, is preferred.

Typical UV-A filters contemplated are:
derivatives of benzoylmethane, such as, for example, 1-(4'-tert-butylphenyl)-3-(4'-methoxyphenyl)propane-1,3-dione, 4-tert-butyl-4'-methoxydibenzoylmethane or 1-phenyl-3-(4'-isopropylphenyl)propane-1,3-dione;
aminohydroxy-substituted derivatives of benzophenones, such as, for example, N,N-diethylaminohydroxybenzoyl n-hexylbenzoate.

The UV-A and UV-B filters can of course also be used in mixtures.

Suitable UV filter substances are specified in the table below.

| No. | Substance | CAS No. (=acid) |
|---|---|---|
| 1 | 4-Aminobenzoic acid | 150-13-0 |
| 2 | 3-(4'-Trimethylammonium)benzylidenebornan-2-one methyl sulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | 2-Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Sulfobenzylidene)bornan-2-one and salts | 58030-58-6 |
| 14 | 3-Benzylidenebornan-2-one | 16087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 3-Imidazol-4-ylacrylic acid and its ethyl ester | 104-98-3 |
| 18 | Ethyl 2-cyano-3,3-diphenylacrylate | 5232-99-5 |
| 19 | 2'-Ethylhexyl 2-cyano-3,3-diphenylacrylate | 6197-30-4 |

-continued

| No. | Substance | CAS No. (=acid) |
|---|---|---|
| 20 | Menthyl o-aminobenzoate or: 5-methyl-2-(1-methylethyl) 2-aminobenzoate | 134-09-8 |
| 21 | Glyceryl p-aminobenzoate or: 1-glyceryl 4-aminobenzoate | 136-44-7 |
| 22 | 2,2'-Dihydroxy-4-methoxybenzophenone (dioxybenzone) | 131-53-3 |
| 23 | 2-Hydroxy-4-methoxy-4-methylbenzophenone (mexenone) | 1641-17-4 |
| 24 | Triethanolamine salicylate | 2174-16-5 |
| 25 | Dimethoxyphenylglyoxalic acid or: sodium 3,4-dimethoxyphenylglyoxalate | 4732-70-1 |
| 26 | 3-(4'-Sulfobenzylidene)bornan-2-one and its salts | 56039-58-8 |
| 27 | 4-tert-Butyl-4'-methoxydibenzoylmethane | 70356-09-1 |
| 28 | 2,2',4,4'-Tetrahydroxybenzophenone | 131-55-5 |
| 29 | 2,2'-Methylenebis[6-(2H-benzotriazol-2-yl)-4-(1,1,3,3-tetramethylbutyl)phenol] | 103597-45-1 |
| 30 | 2,2'-(1,4-Phenylene)bis-1H-benzimidazole-4,6-disulfonic acid, Na salt | 180898-37-7 |
| 31 | 2,4-bis-[4-(2-Ethylhexyloxy)-2-hydroxy]phenyl-6-(4-methoxyphenyl)-(1,3,5)-triazine | 187393-00-6 |
| 32 | 3-(4-Methylbenzylidene)camphor | 36861-47-9 |
| 33 | Polyethoxyethyl 4-bis(polyethoxy)paraaminobenzoate | 113010-52-9 |
| 34 | 2,4-Dihydroxybenzophenone | 131-56-6 |
| 35 | 2,2'-Dihydroxy-4,4'-dimethoxybenzophenone-5,5'-disodium sulfonate | 3121-60-6 |
| 36 | Benzoic acid, 2-[4-(diethylamino)-2-hydroxybenzoyl]hexyl ester | 302776-68-7 |
| 37 | 2-(2H-Benzotriazol-2-yl)-4-methyl-6-[2-methyl-3-[1,3,3,3-tetramethyl-1-[(trimethylsilyl)oxy]disiloxanyl]propyl]phenol | 155633-54-8 |
| 38 | 1,1-[(2,2'-Dimethylpropoxy)carbonyl]-4,4-diphenyl-1,3-butadiene | 363602-15-7 |

Besides the two aforementioned groups of primary photoprotective substances, it is also possible to use secondary photoprotective agents of the antioxidant type, which interrupt the photochemical reaction chain which is triggered when UV radiation penetrates into the skin. Typical examples thereof are tocopherols (vitamin E) and oil-soluble ascorbic acid derivatives (vitamin C).

According to the invention, suitable derivatives (salts, esters, sugars, nucleotides, nucleosides, peptides and lipids) of said compounds can be used as effector molecules.

Preference is further given to so-called peroxide decomposers, i.e. compounds which are able to decompose peroxides, particularly preferably lipid peroxides. These are understood to include organic substances, such as, for example, 5-pyrimidinol derivatives and 3-pyridinol derivatives and probucol.

Furthermore, said peroxide decomposers are preferably the substances described in the patent applications WO/0207698 and WO/03059312, to whose contents reference is hereby expressly made, preferably the boron-containing or nitrogen-containing compounds described therein, which are able to reduce peroxides or hydroperoxides to the corresponding alcohols without formation of free-radical conversion products. Sterically hindered amines can also be used for this purpose.

A further group are antiirritants, which have an antiinflammatory effect on skin damaged by UV light. Such substances are, for example, bisabolol, phytol and phytantriol.

A further group of poorly water-soluble effector substances are active substances which can be used in crop protection, for example herbicides, insecticides and fungicides.

Furthermore suitable as poorly water-soluble effect substances are active substances for pharmaceutical use, in particular those for oral administration. The method according to the invention can in principle be used on a large number of active substances irrespective of the medical indication.

Examples of suitable poorly water-soluble pharmaceutical active substances are given in the table below.

| Active substance | Empirical formula | Solubility in water [g/L] |
|---|---|---|
| Felodipine | $C_{18}H_{19}Cl_2NO_4$ | 4.53E−03 (22° C.) |
| Indomethacin | $C_{19}H_{16}ClNO_4$ | 1.4E−02 (25° C.) |
| Piroxicam | $C_{15}H_{13}N_3O_4S$ | 2.3E−02 (RT) |
| Carbamazipine | $C_{15}H_{12}N_2O$ | 9.451E−01 (RT) |
| 17--Estradiol | $C_{18}H_{24}O_2$ | 1.836E−05 (25° C.) |
| Clotrimazole | $C_{22}H_{17}ClN_2$ | <1.0E−02 (25° C.) |
| Ketoconazole | $C_{26}H_{28}Cl_2N_4O_4$ | 8.0E−02 (37° C.) |
| Cinnarizine | $C_{26}H_{28}N_2$ | 7.5E−01 |
| Griseofulvin | $C_{17}H_{17}ClO_6$ | 3.685E−05 (25° C.) |
| Ibuprofen | $C_{13}H_{18}O_2$ | 2.1E−02 (25° C.) |

(iii) Formulation of Hydrophobic Active Substances

Formulations of poorly water-soluble active substances can be prepared using amphiphilic, self-assembling proteins in various ways. Poorly water-soluble, hydrophobic active substances can be packed in protein microbeads or be stabilized in a colloidally-disperse manner through protein coating, which can be achieved, for example, in micronization batches. The formulation of hydrophobic active substances can take place through inclusion in microbeads. This process comprises two steps. In the first step, the hydrophobic active substance and the amphiphilic, self-assembling protein are dissolved in a common phase. For this, the active substance and the protein can be dissolved directly by a solvent or a solvent mixture. Alternatively, the active substance and the protein can firstly be dissolved in different solvents and the solutions then mixed together, thus again producing a common phase. The common phase may be a molecularly disperse phase or a colloidally disperse phase.

Dissolution of the hydrophobic active substance and of the protein in different solvents and the subsequent mixing of the two solutions is particularly advantageous when the hydrophobic active substance and the protein cannot be dissolved in a common solvent or solvent mixture. In this way, through this process, it is possible to also prepare colloidally disperse solutions of hydrophobic active substances by diluting the active substance dissolved in a suitable solvent in another solvent in which the active substance is insoluble.

Since proteins are generally readily water-soluble, preference is given to working with aqueous solutions and mixtures of water and water-miscible, organic solvents. Examples of suitable, water-miscible solvents are alcohols, such as methanol, ethanol and isopropanol, fluorinated alcohols, such as hexafluoroisopropanol and trifluoroethanol, alkanones, such as acetone, and also sulfoxides, such as, for example, dimethyl sulfoxide, or formamides, such as dimethylformamide, or other organic solvents, such as, for example, tetrahydrofuran and acetonitrile or N-methyl-2-pyrrolidone. In general, it is possible to work with all solvents and solvent mixtures in which the proteins can be dissolved. Examples of suitable solvents are fluorinated alcohols, such as, for example, hexafluoroisopropanol or trifluoroethanol, ionic liquids, such as, for example, EMIM acetate, aqueous solutions of chaotropic salts, such as, for example, urea, guanidinium hydrochloride and guanidinium thiocyanate, or organic acids, such as, for example, formic acid, and mixtures of these solvents with other organic solvents. Examples of solvents which can be mixed with the solvents for the protein are, inter alia, alcohols such as methanol, ethanol and isopropanol, alkanones, such as acetone, sulfoxides, such as, for example, dimethyl sulfoxide, formamides, such as dimethylformamide, haloalkanes, such as methylene chloride, and also further organic solvents, such as, for example, tetrahydrofuran.

The second step of the formulation of hydrophobic active substances in microbeads is phase separation into a phase low in protein and active substance and into a phase rich in protein and active substance, which subsequently hardens. Here, the hydrophobic active substance is incorporated into the assembly form of the protein. On account of surface effects during phase separation, preferably round protein structures, so-called microbeads, are formed.

Phase separation is preferably induced by adding aqueous solutions of lyotropic salts to the mixtures of proteins and hydrophobic active substances. Suitable lyotropic salts are described by the Hofmeister series. Ammonium sulfate and potassium phosphate are particularly suitable. The addition of these solutions can take place by simple mixing, dropwise addition or through dialysis.

The interactions between the hydrophobic active substance and the protein are based essentially on their hydrophobic properties, although hydrogen bonds, ionic interactions and van der Weals interactions may also be involved. The hydrophobic active substance can be bound to the surface, incorporated into the microbeads or else be associated with the microbeads in both ways. The binding of the hydrophobic active substance to the microbeads can be determined by the depletion in the assembly mixture of dissolved active substance. The concentration of the active substance can be measured by a quantitative analysis of its properties. Thus, the binding of photoabsorbing active substances can be analyzed, for example, by photometric methods. For this, for example, the coloration of the microbeads or the decoloration of the phase low in protein and active substance in the formulation mixture are determined by measuring the absorption of a colored active substance. Using these methods it is also possible to determine how high the active substance content in the microbeads is.

Release of the active substances from the microbeads can take place by desorption in suitable solvents, as a result of the degradation of the microbeads by proteases or through dissolution of the microbeads by suitable solvents. Suitable solvents for the desorption are all solvents or solvent mixtures in which the active substance can be dissolved. Suitable proteases can be added as technical-grade proteases to a suspension of protein microbeads in a targeted manner, or occur naturally at the desired active site of the effector molecules, such as, for example, skin proteases, proteases of the digestive tract, e.g. stomach or intestine proteases, or proteases released from microorganisms. Solvents which can dissolve the microbeads are, for example, fluorinated alcohols, such as, for example, hexafluoroisopropanol or trifluoroethanol, ionic liquids, such as, for example, EMIM acetate, aqueous solutions of chaotropic salts, such as, for example, urea, guanidinium hydrochloride and guanidinium thiocyanate, or organic acids, such as, for example, formic acid, and mixtures of these solvents with other organic solvents. The rate and the kinetics of the release of the effector molecules can be controlled, for example, through the charge density with active substances and the size of the microbeads and/or their ratio of volume to surface area.

The formulation of poorly water-soluble hydrophobic active substance can also take place through stabilization of its colloidally disperse solution, e.g. through micronization.

The invention further provides the use of the protein microbeads produced using the described amphiphilic, self-assembling proteins, or of the colloidally disperse protein formulations produced, for example, by micronization, for the storage, transportation or release of active substances in pharmaceutical products, cosmetic products, crop protection products, foods and animal feeds. In this connection, the protein microbeads further serve, for example, to protect the packed active substances against environmental influences, such as, for example, oxidative processes or UV radiation, or against destruction as a result of reaction with other constituents of the products, or against degradation by certain proteases. The active substance can be released from the protein microbeads or colloidally disperse protein formulations by desorption, proteolytic degradation, targeted release or slow release or combination of these mechanisms.

Preference is given to protein microbeads and active substances formulated therewith in pharmaceutical products for peroral administration. In this connection, the stability of the active ingredients can be increased upon passage through the stomach since no proteolytic degradation of the protein microbeads takes place under the conditions prevailing therein. Release of the active substances from the perorally administered active substance-comprising microbeads then takes place in the intestine. Topical applications of the protein microbeads and of the pharmaceutical active substances embedded therein are also possible. Degradation of the protein microbeads and the release of the active substances resulting therefrom is then controlled by proteases present on the skin and/or in the upper skin layers.

In pharmaceutical products, foods and animal feeds and crop protection products, a formulation of active substances with the described amphiphilic, self-assembling proteins can furthermore lead to increased bioavailability of the active substances. The packaging of pharmaceutical active substances in protein microbeads or the colloidally disperse formulation of active substances using the described amphiphilic, self-assembling proteins can also lead to the active substance being better able to overcome the blood-brain barrier or to improved absorption via the intestinal mucosa. Crop protection products can be protected from washing processes through encapsulation and/or embedding in protein microbeads. Certain active substance particle sizes which are better absorbed and/or have better bioavailability can be established by packing in protein microbeads or through colloidally disperse formulation, e.g. by micronization mixtures using amphiphilic, self-assembling proteins.

By varying the amino acid sequence of the described amphiphilic, self-assembling proteins and/or through fusion with additional protein or peptide sequences, it is possible to generate structures which specifically recognize certain surfaces, e.g. skin, hair, leaves, roots or intestine surfaces or blood vessel surfaces and/or are recognized and bound by these surfaces or the receptors present.

As a result, it is possible to bring the active substances formulated with the described amphiphilic, self-assembling proteins more effectively to the desired active site and/or to improve the absorption of active substances. The bioavailability of pharmaceutical active substances or active substances in foods and animal feeds can be increased if these are packed in protein microbeads which are additionally present in fused and/or associated form with proteins which bind to certain surface markers (e.g. receptors) of cells in the intestinal tract (e.g. mucosa cells). Such proteins are, for example, the MapA protein or the collagen-binding protein CnBP from Lactobacillus reuteri (Miyoshi et at, 2006, Biosci. Biotechnol. Biochem. 70:1622-1628) or functionally comparable proteins from other microorganisms, primarily natural gastrointestinal flora. The described binding proteins mediate adhesion of the microorganisms to cell surfaces. As a result of coupling and/or fusion of the binding proteins to the described amphiphilic, self-assembling proteins, active substance-containing protein microbeads resulting therefrom would be directed in a more targeted way to corresponding absorption sites and/or reside longer at these sites, which results in extended and improved active substance release and absorption.

Furthermore, by varying the amino acid sequence of the amphiphilic, self-assembling proteins described for the active substance formulation and/or fusion with additional protein or peptide sequences, it is possible to direct active substances in a targeted manner to desired active sites in order thus to achieve, for example, higher specificity, lower active substance consumption or active substance dose, or a more rapid or stronger effect.

EXPERIMENTAL SECTION

Example 1

Packing of β-carotene from THF and THF/isopropanol in Microbeads and Release by Proteolysis Preparation of the β-carotene Solutions A stock solution was prepared by dissolving 80 mg of β-carotene and 16 mg of tocopherol in 10 g of THF. The solutions 1-4 were then prepared from this stock solution by dilution corresponding to table 1.1.

All of the solutions were prepared shortly before use and further processed immediately after dilution.

TABLE 1.1

β-carotene solutions

| β-Carotene solution | Solution | Concentration (mg/ml) |
|---|---|---|
| 1 | 1/30 dilution in isopropanol | 0.3 |
| 2 | 1/10 dilution in isopropanol | 0.9 |
| 3 | 1/30 dilution in THF | 0.3 |
| 4 | 1/10 dilution in THF | 0.9 |

Packing of β-carotene in microbeads by direct addition of potassium phosphate.

In order to pack β-carotene into the C16 protein microbeads, a common phase of C16 protein and β-carotene was firstly prepared. For this, in each case 500 μl of a solution of 10 mg/ml of C16 protein in 5 mM potassium phosphate, pH 8 were mixed with 50 μl or 100 μl of the β-carotene solutions (solutions 1-4) (Tab. 1.2). In the case of the batches with β-carotene from THF/isopropanol (batches 1-4), orange dispersions were obtained; in the case of the batches with β-carotene from THF (batches 5-8), yellow dispersions were obtained.

In order to induce the C16 protein microbead formation through phase separation, 1000 μl of a 1 M potassium phosphate solution, pH 8.0 were added to each of the batches (Tab. 1.2). After incubation for 15 min at room temperature, the batches were separated by centrifugation into a markedly colored pellet of C16 protein microbeads containing β-carotene and colorless supernatant. The β-carotene used was thus transferred completely to the microbeads during phase separation. The colorless supernatant was separated off. The pellets were then washed twice with distilled water and redispersed.

Following redispersion of the C16 protein microbeads, in the case of the batches containing the β-carotene solutions from THF/isopropanol (batches 1-4), orange dispersions were obtained, and, in the case of the batches containing the β-carotene solutions from THF (batches 5-8), yellow dispersions were obtained.

TABLE 1.2

Packing of β-carotene from THF and THF/isopropanol in C16 protein microbeads by adding 1M potassium phosphate solution

| Batch | C16 (10 mg/ml) [μl] | Solution 1 [μl] | Solution 2 [μl] | 1M potassum phosphate [μl] |
|---|---|---|---|---|
| 1 | 500 | 50 | — | 1000 |
| 2 | 500 | 100 | — | 1000 |
| 3 | 500 | — | 50 | 1000 |
| 4 | 500 | — | 100 | 1000 |
| Batch | C16 (10 mg/ml) [μl] | Solution 3 [μl] | Solution 4 [μl] | 1M potassium phosphate [μl] |
| 5 | 500 | 50 | — | 1000 |
| 6 | 500 | 100 | — | 1000 |
| 7 | 500 | — | 50 | 1000 |
| 8 | 500 | — | 100 | 1000 |

Packing of β-carotene in C16 protein microbeads by dialysis against potassium phosphate Alternatively to the direct addition of potassium phosphate to the common phase of β-carotene and C16 protein, phase separation can also take place through dialysis against 1 M potassium phosphate. Since the dialysis was carried out in dialysis tubes, 10 times the batch volume compared to the direct addition of the potassium phosphate solution was pipetted in each case (Tab. 1.3).

TABLE 1.3

Packing of β-carotene from THF and THF/isopropanol in C16 protein microbeads by dialysis against 1M potassium phosphate solution

| Batch | C16 (10 mg/ml) [ml] | Solution 1 [ml] | Solution 2 [ml] |
|---|---|---|---|
| D1 | 5 | 0.5 | — |
| D2 | 5 | 1 | — |

TABLE 1.3-continued

Packing of β-carotene from THF and THF/isopropanol in C16 protein microbeads by dialysis against 1M potassium phosphate solution

| | | | |
|---|---|---|---|
| D3 | 5 | — | 0.5 |
| D4 | 5 | — | 1 |

| Batch | C16 (10 mg/ml) [ml] | Solution 3 [ml] | Solution 4 [ml] |
|---|---|---|---|
| D5 | 5 | 0.5 | — |
| D6 | 5 | 1 | — |
| D7 | 5 | — | 0.5 |
| D8 | 5 | — | 1 |

For this, the C16 solution (10 mg/ml in 5 mM potassium phosphate, pH 8.0) was mixed with the particular β-carotene solution and the mixture was then immediately placed into the dialysis tube and dialyzed against 1 M potassium phosphate solution. After overnight dialysis, the microbead dispersion was removed from the tubes and separated by centrifugation into a colorless supernatant and into a colored pellet. As also in the case of the direct addition of potassium phosphate to the common phase of C16 protein and β-carotene, the β-carotene was bound quantitatively by the C16 protein in the form of the protein microbeads. The colorless supernatant was separated off. The pellets were subsequently washed twice with distilled water and then redispersed.

Figure 1:
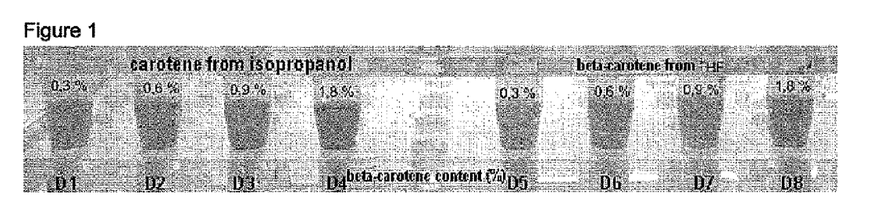
FIG. 1: Dispersions of the C16 protein microbeads with β-carotene from THF and THF/isopropanol in water. From left to right: batches Dl-D4 (THF/isopropanol) and batches D5-D8 (THF). The content of β-carotene in the C16 protein microbeads is quoted as percent by weight based on the weight of the C16 protein microbeads.

Following redispersion of the protein microbeads, in the case of the batches containing the β-carotene solutions from THF/isopropanol (batches D1-D4), orange dispersions were obtained, and, in the case of the batches containing the β-carotene solution THF (batches D5-D8), yellow dispersions were obtained (FIG. 1).

FIG. 1: Dispersions of the C16 protein microbeads with β-carotene from THF and THF/isopropanol in water. From left to right: batches D1-D4 (THF/isopropanol) and batches D5-D8 (THF). The content of β-carotene in the C16 protein microbeads is quoted as percent by weight based on the weight of the C16 protein microbeads.

Figure 2:
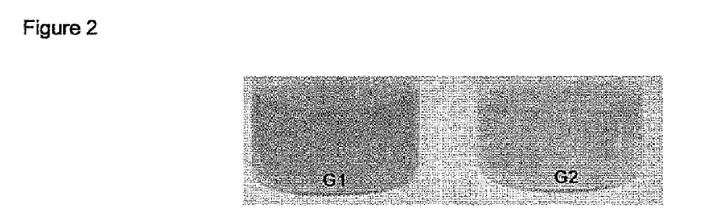
FIG. 2: Dispersions of the C16 protein microbeads containing β-carotene from THF/isopropanol (0.9 percent by weight of β-carotene, batch G1, left) and THF (0.3 percent by weight of β-carotene, batch G2, right).

In order to reproduce the different colorations of the C16 protein microbeads containing β-carotene from THF and THF/isopropanol, batches D4 and D5 were repeated on a larger scale (Tab. 1.4). Again, with β-carotene from THF, yellow C16 protein microbeads were obtained, and, with β-carotene from THF/isopropanol, orange C16 protein microbeads were obtained (FIG. 2).

TABLE 1.4

Packing of β-carotene from THF and THF/isopropanol in C16 protein microbeads by dialysis against 1M potassium phosphate solution

| Batch | C16 (10 mg/ml) [ml] | Solution 2 [ml] | Solution 3 [ml] |
|---|---|---|---|
| G1 | 50 | 5 | — |
| G2 | 50 | — | 5 |

FIG. 2: Dispersions of the C16 protein microbeads containing β-carotene from THF/isopropanol (0.9 percent by weight of β-carotene, batch G1, left) and THF (0.3 percent by weight of β-carotene, batch G2, right).

Release of β-carotene from C16 protein microbeads by digestion with proteinase K In order to show that the β-carotene in the C16 protein microbeads can be released by proteolysis, 200 μl of the microbead dispersions G1 and G2 in water were mixed with 500 μl of 5 M potassium phosphate pH 8.0. 5 μl of proteinase K (Roche, 19.45 mg/ml) were then added and the mixture was incubated overnight at room temperature. The control used in each case was a mixture of the C16 protein microbead dispersions without proteinase K. Following overnight incubation, the mixture was centrifuged. In the presence of the protease, the C16 protein microbeads were digested and the β-carotene was released. After the centrifugation, no pellet was visible. The supernatant was highly colored. Without protease, the intact C16 protein microbeads could be centrifuged off. A markedly colored pellet was observed. The supernatant was colorless.

Figure 3:
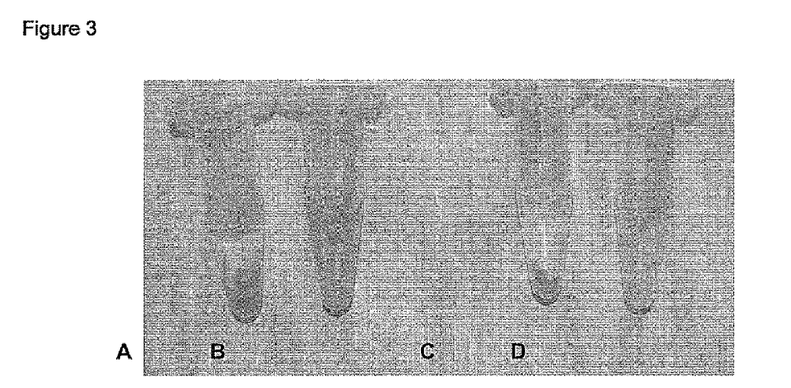
FIG. 3: Digestion of the C16 protein microbead dispersions by proteinase K. A) C16 protein microbeads containing β-carotene from THF/isopropanol (0.9 percent by weight of β-carotene, batch G1) without protease; B) C16 protein microbeads containing β-carotene from THF/isopropanol (0.9 percent by weight of β-carotene, batch G1) with protease; C) C16 protein microbeads containing β-carotene from THF (0.3 percent by weight of β-carotene, batch G2) without protease; D) C16 protein microbeads containing β-carotene from THF (0.3 percent by weight of β-carotene, batch G2) with protease.

FIG. 3 Digestion of the C16 protein microbead dispersions by proteinase K. A) C16 protein microbeads containing β-carotene from THF/isopropanol (0.9 percent by weight of β-carotene, batch G1) without protease; B) C16 protein microbeads containing β-carotene from THF/isopropanol (0.9 percent by weight of β-carotene, batch G1) with protease; C) C16 protein microbeads containing β-carotene from THF (0.3 percent by weight of β-carotene, batch G2) without protease; D) C16 protein microbeads containing β-carotene from THF (0.3 percent by weight of β-carotene, batch G2) with protease.

Example 2

Stability of β-carotene-comprising Microbeads and Release of β-carotene from Microbeads by Proteolytic Digestion By treating β-carotene-comprising C16 protein microbeads with different proteases which are active in the human stomach and/or intestine, the aim was to demonstrate the suitability of protein microbeads as storage, transportation and/or delivery system for pharmacological effect substances.

To prepare β-carotene-containing C16 protein microbeads, 80 mg of β-carotene and 16 mg of vitamin E were dissolved in 10 ml of THF and then diluted with 90 ml of isopropanol. Part of this solution was then mixed with 10 volumes of C16 protein solution (10 mg/ml in 5 mM potassium phosphate buffer pH 8). The mixture was then admixed with 2 volumes of 1 M potassium phosphate buffer pH 8. The resulting β-carotene-comprising C16 protein microbeads were centrifuged off and excess free β-carotene was removed by washing the sediment with water.

Figure 4:
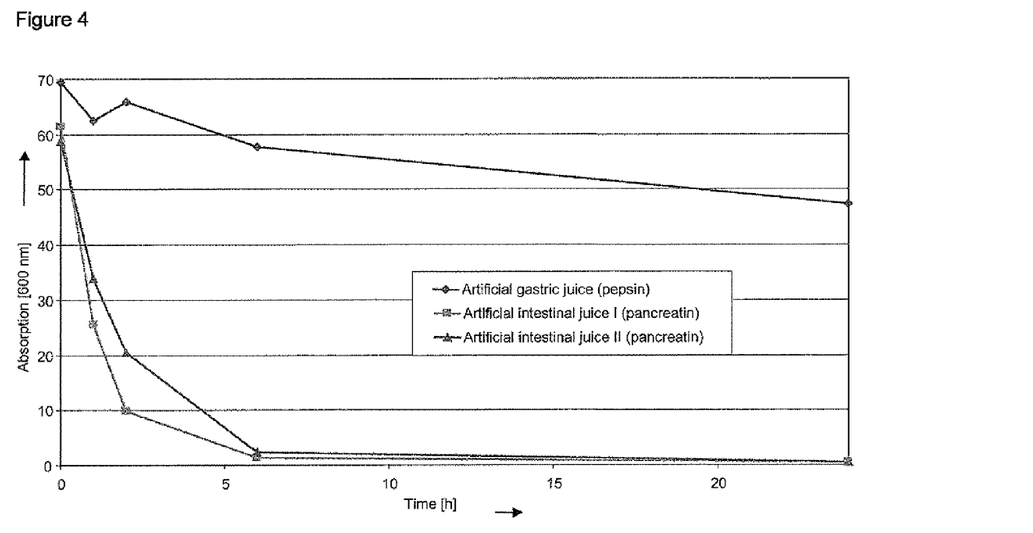
FIG. 4: Determination of intact C16 protein microbeads by photometric measurement of the absorption at 600 nm.

20 mg of β-carotene-comprising C16 protein microbeads were resuspended with 2 ml of synthetic gastric juice (6.4 mg of pepsin, 80 mM HCl, 4 mg of NaCl) or 2 ml of synthetic intestinal juice I (20 mg of pancreatin, 0.45 M sodium phosphate pH 7.5, 0.9 mM sodium taurocholate) or 2 ml of synthetic intestinal juice II (20 mg of pancreatin, 0.45 M sodium phosphate pH 7.5, 6 mM sodium taurocholate) and incubated at 37° C. for 0, 1, 2, 6, 24 and 48 h with shaking (140 rpm). C16 protein microbeads which had not been degraded proteolytically were determined via the scattering of the suspension at 600 nm (FIG. 4). Intact C16 protein microbeads were then centrifuged off and the β-carotene content in the supernatant was analyzed through determination of the absorption at 445 nm (FIG. 5).

Figure 5:
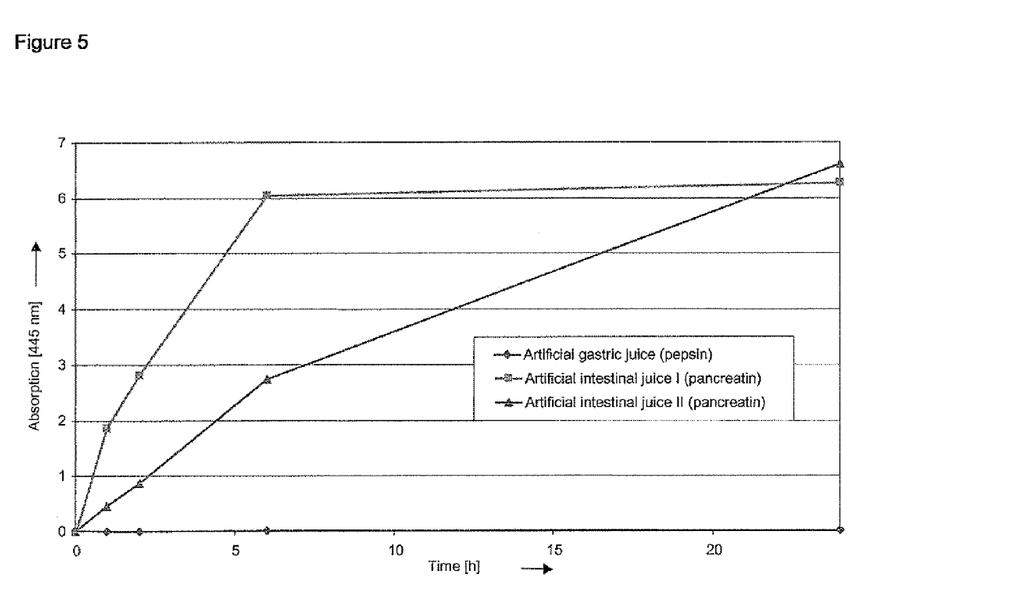
FIG. 5: Determination of the β-carotene released from C16 protein microbeads by photometric absorption measurement at 445 nm.

As a result of treatment with pepsin-containing synthetic gastric juice, even after 48 h, C16 protein microbeads could barely be degraded (FIG. 4) and thus β-carotene released (FIG. 5). On the other hand, on treatment with pancreatin-containing synthetic intestinal juice I and II, C16 protein microbeads were degraded virtually completely within just 6 h (FIG. 4) and the β-carotene present was released (FIG. 5). Accordingly, C16 protein microbeads would withstand passage through the human stomach without significant degradation and only release the bound effector substances as a result of proteolytic degradation in the intestinal tract.

FIG. 4: Determination of intact C16 protein microbeads by photometric measurement of the absorption at 600 nm.

FIG. 5: Determination of the β-carotene released from C16 protein microbeads by photometric absorption measurement at 445 nm.

Example 3

Figure 6:
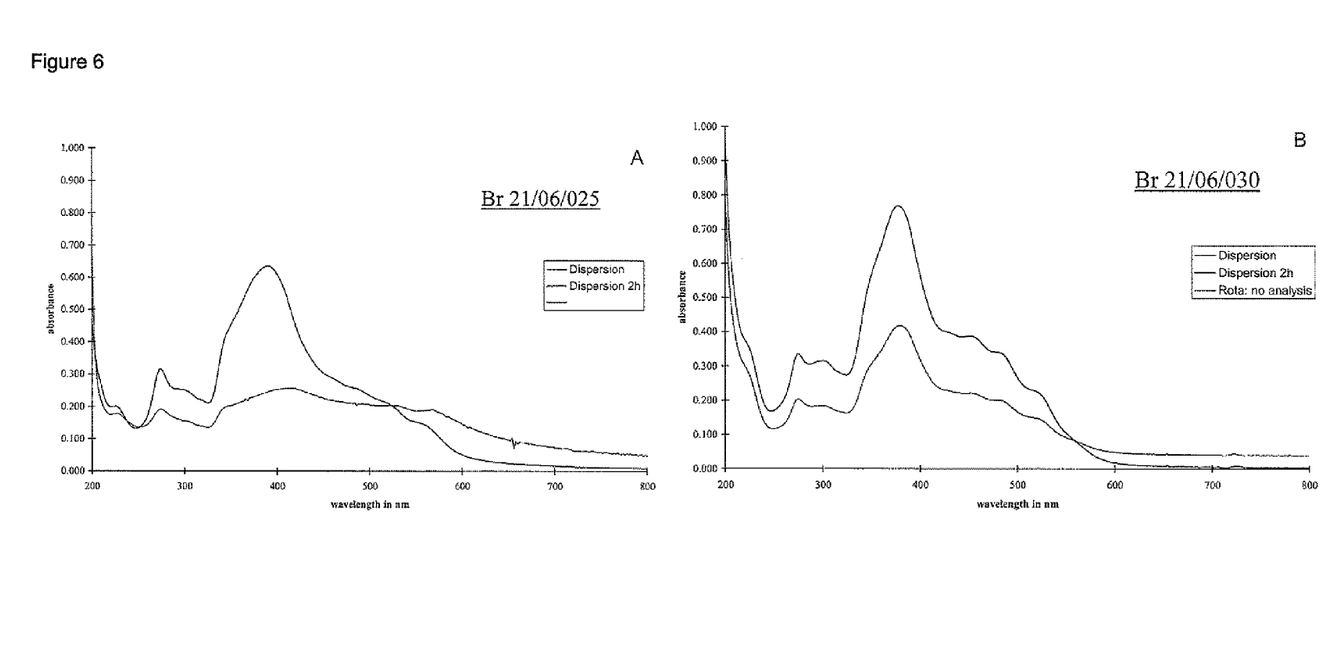
FIG. 6: Formulation of lycopene with C16 spider silk protein. Absorption of untreated lycopene sample (A) and lycopene sample treated with C16 protein (B) directly after mixing (black graph) and 2 hours after mixing (red graph).
Figure 7:
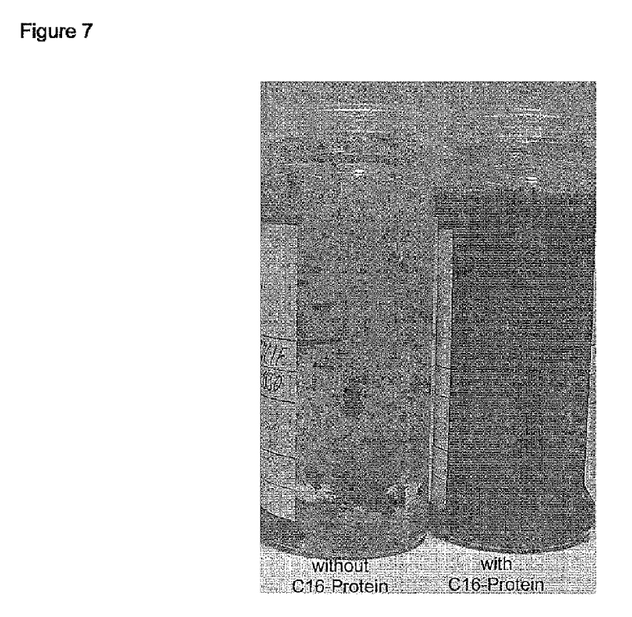
FIG. 7: Formulation of lycopene with C16 spider silk protein. Comparison of untreated lycopene dispersion (left) with a C16 protein-stabilized lycopene dispersion (right) approximately 30 days after mixing.

Micronization with C16 Spider Silk Protein 2 g of crystalline lycopene and 0.4 g of alpha-tocopherol were dissolved in 500 g of THF. The active substance solution was continuously mixed at room temperature and a flow rate of 2.42 g/min with an aqueous solution consisting of 0.2 g/l of C16 protein in 5 mM potassium phosphate buffer (pH 8), and a flow rate of 25.4 g/min. The active substance particles that formed upon mixing in the THF/water mixture had a particle size of 103 nm. After 2 hours, a clear dispersion stabilization of the sample treated with C16 protein (FIG. 6B) compared to the untreated sample (FIG. 6A) was found. Even after several days, the lycopene dispersion with C16 protein appeared stable, whereas the untreated lycopene dispersion flocculated to a great extent (FIG. 7). Some of the lycopene dispersion stabilized with C16 protein was concentrated to a solids content of 0.28%. In this state, dried lycopene was poorly redispersible. Alternatively, a lycopene dispersion stabilized with C16 protein was treated with 330 mM potassium phosphate (final concentration in the mixture) and dried. The resulting lycopene powder was readily redispersible.

FIG. 6: Formulation of lycopene with C16 spider silk protein. Absorption of untreated lycopene sample (A) and lycopene sample treated with C16 protein (B) directly after mixing (black graph) and 2 hours after mixing (red graph).

FIG. 7: Formulation of lycopene with C16 spider silk protein. Comparison of untreated lycopene dispersion (left) with a C16 protein-stabilized lycopene dispersion (right) approximately 30 days after mixing.

Example 4

Packing of Metazachlor from Isopropanol in Microbeads and Release by Proteolysis Poorly water-soluble plant active substances can be packed in protein microbeads which are prepared from amphiphilic, self-assembling proteins and can then also be released therefrom. For this, the nonlimiting example chosen was the herbicide active substance metazachlor.

500 μl of a 10 mg/ml C16 protein-comprising potassium phosphate solution (5 mM, pH 8.0) were mixed with 100 μl of a metazachlor solution (50 mg/ml in isopropanol). C16 Protein microbead formation was induced by adding 1 ml of 1 M potassium phosphate buffer (pH 8.0). The mixture was incubated for 1 h at room temperature and then centrifuged for 10 min at 20000×g. The pellet was washed twice with 5 ml of double-distilled $H_2O$ and then lyophilized. An identical mixture without C16 protein was carried out as control.

Following precipitation with potassium phosphate, microbeads formed in the mixture with C16 protein and metazachlor. These were morphologically comparable with those of a standard mixture with C16 protein but without active substance. In the C16 metazachlor mixture, no metazachlor crystals were visible. In the mixture of metazachlor without C16 protein, on the other hand, large active substance crystals were formed. This illustrates that the C16 protein has a significant inhibitiory effect on the crystallization of metazachlor in the presence of aqueous potassium phosphate buffer.

Determination of the metazachlor concentration in the supernatant following C16 protein precipitation or C16 microbead formation revealed that approximately 90% of the active substance was present in packed form in the protein microbeads and/or in associated form with these. In each case, about 20% of the active substance were present in the wash supernatants.

The lyophilized metazachlor-comprising C16 protein microbeads were proteolytically digested in 1 ml of 10 mM Tris buffer; 0.1% SDS; 100 μg of proteinase K for 1 h at 37° C. The active substance crystals remaining from the mixture after centrifugation for 10 minutes (20000×g) were dissolved in 500 μl of isopropanol. About 11% of the amount of metazachlor used was detected in the supernatant of the protease digestion. The active substance crystals redissolved in isopropanol constituted about 35% of the amount of metazachlor used.

Analysis of the Active Substance Distribution (Photometric Determination at λ=215 nm)

|  | Amount of substance [mg] |
|---|---|
| Amount of metazachlor used | 5.0 |
| Supernatant after potassium phosphate precipitation | 0.58 |
| Wash supernatant 1 | 0.93 |
| Wash supernatant 2 | 0.93 |
| Supernatant after protease digestion | 0.55 |
| Pellet after digestion in isopropanol | 1.74 |
| Sum of the determined AS amounts | 4.73 |

Example 5

Packing and Stabilization of Retinol in Protein Microbeads

Poorly water-soluble or water-insoluble active substances which are labile toward influences such as oxygen radicals, UV etc. can be packed in protein microbeads which are prepared from amphiphilic, self-assembling proteins. They can also subsequently be released again therefrom. Additionally, as a result of formulation and/or packing in protein microbeads, the active substances are protected against the harmful influences and degradation resulting therefrom. In order to show this, the nonlimiting example chosen was the active substance retinol, which was packed in C16 protein microbeads and stirred while sparging with air and with homogeneous mixing for several hours. At various time points, samples were taken and the remaining retinal was quantified following THF extraction.

The batches shown in Table 5.1 were investigated. For this, the retinol-THF solution in isopropanol was firstly diluted, then admixed with the aqueous C16 protein solution and then, in the case of batch 1, the C16 protein microbead formation was induced by adding 1 M potassium phosphate solution. Since the presence of cations, e.g. through potassium phosphate in the C16 protein packing batch, contributes in principle to the increase in the oxidation of freely dissolved retinal or retinal occurring in particulate form, a 154 mM sodium chloride solution was added in control batches with and without C16 spider silk protein, but in which no C16 protein microbead formation was to be induced (see Fisher et al., 1972, Biochem. J. 132: 259-270). The batches were incubated in glass vessels closable with plastic lids with stirring on a magnetic stirrer and with continuous sparging via a cannula for up to 7 hours. For sampling, in each case 4×300 µl were taken, in each of which, by calculation, a maximum of 9.38 µg of retinal should be present. Following removal, the C16 microbeads of the packing batch were centrifuged off and the resulting retinal was extracted with 1.5 ml of THF and quantified by absorption photometry at 325 nm. In the case of the batches without C16 microbeads, 1.5 ml of THF was added directly to the 300 µl sample, the sample was mixed and centrifuged in order to generate phase separation. The retinol then present in the upper THF phase was likewise quantified by means of absorption photometry at 325 nm.

TABLE 5.1

Various batches for quantifying the C16 spider silk protein-mediated oxidation stability of retinol.

| Batch 1: Packing batch | 0.9 ml isopropanol (Sigma, crystalline) |
| --- | --- |
| | 0.1 ml retinol 5 mg/ml in THF |
| | 5 ml C16 solution 10 mg/ml in |
| | 5 mM K2HPO$_4$ buffer |
| | 10 ml 1M K$_2$HPO$_4$ buffer |
| Batch 2: Stabilization batch "Coating" | 0.9 ml isopropanol (Sigma, crystalline) |
| | 0.1 ml retinol 5 mg/ml in THF |
| | 5 ml C16 solution 10 mg/ml in |
| | 5 mM K$_2$HPO$_4$ buffer |
| | 10 ml 154 mM NaCl solution |
| Batch 3: Control batch without C16 protein | 0.9 ml isopropanol (Sigma, crystalline) |
| | 0.1 ml retinol 5 mg/ml in THF |
| | 5 ml 5 mM K$_2$HPO$_4$ buffer |
| | 10 ml 154 mM NaCl solution |

Figure 8:
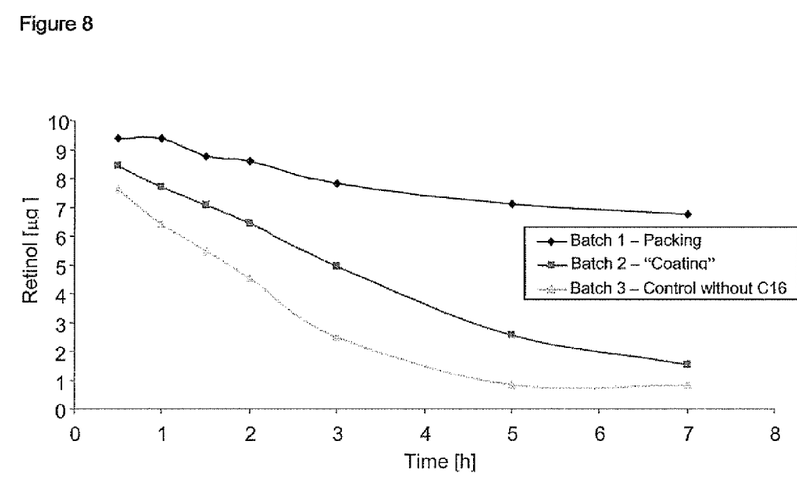
FIG. 8: Determination of the retinol stability in C16 formulation batches as a function of the incubation time.

In the courses of the batches with C16 spider silk protein (batch 1—packing in C16 microbeads, batch 2—soluble C16), compared to the control without C16 protein, a significant stabilization of retinol under atmospheric oxygen is observed (Tab. 5.2; FIG. 8). Whereas in batch 2 the amount of retinal also significantly reduces after 5-7 h, in batch 1 in which the active ingredient has been packed into C16 microbeads, more than 70% of intact retinol can be detected even after 7 h (Tab. 5.2; FIG. 8). Accordingly, the packing of retinol in C16 protein microbeads appears to be a suitable method by which stabilization against oxygen radical-induced degradation can be achieved. As a result of proteolytic degradation of the retinol-laden C16 microbeads with proteinase K (2.25 U) in 1 ml of 5 mM potassium phosphate buffer pH 8, the active ingredient could be released.

TABLE 5.2

Determination of the retinol stability in C16 formulation batches.

| Time [h] | Retinol [µg] batch 1 | Retinol [µg] batch 2 | Retinol [µg] batch 3 |
| --- | --- | --- | --- |
| 0.5 | 9.37 | 8.42 | 7.61 |
| 1 | 9.37 | 7.68 | 6.41 |
| 1.5 | 8.74 | 7.06 | 5.43 |
| 2 | 8.58 | 6.44 | 4.52 |
| 3 | 7.79 | 4.95 | 2.49 |
| 5 | 7.12 | 2.54 | 0.81 |
| 7 | 6.75 | 1.53 | 0.82 |

FIG. 8: Determination of the retinol stability in C16 formulation batches as a function of the incubation time.

In order to determine the maximum loading density of the C16 microbeads with active substance, varying amounts of retinol were used in packing batches (see batch 1). The solvent used for the active substance here was exclusively THF. The C16 protein microbead formation was then induced by adding 1M potassium phosphate buffer (pH 8.0). The batch was incubated for 1 h at 10° C. and then centrifuged for 10 min at 20000×g. The pellet was washed twice with distilled water. The active substance was then dissolved out by washing the C16 protein microbeads with 2 ml of THF and quantified by means of absorption photometry at 325 nm (see Tab. 5.3). It was found that the maximum charge density for retinol in this experiment is about 1.9 mg per 5 mg of C16 protein used (Tab. 5.3). In the case of quantitative precipitation to C16 microbeads, the retinol active substance concentration or loading density is accordingly about 38%.

TABLE 5.3

Quantifying the retinol packed in 5 mg of C16 microbeads and released again therefrom.

| Retinol used [µg] | Retinol extracted [µg] |
| --- | --- |
| 0 | 0 |
| 50 | 44.48 |
| 100 | 96.31 |
| 250 | 200.94 |
| 500 | 306.9 |
| 1000 | 603.43 |
| 5000 | 1937.05 |

Example 6

Packing of Ibuprofen from THF in Microbeads and Release by Proteolysis

Poorly water-soluble or water-insoluble pharmacologically active substances can be packed in protein microbeads which are prepared from amphiphilic, self-assembling proteins. They can also then be released therefrom again. In addition, these active substances can be protected by formulation and/or packing in protein microbeads against harmful influences, e.g. certain proteases or strongly acidic pH values and degradation resulting therefrom. Certain active substance particle sizes or active substance structures which are better absorbed and/or have better bioavailability can be established by packing in protein microbeads and/or through micronisation batches using amphiphilic, self-assembling proteins. In order to show this, the active substance ibuprofen [(RS)-2-(4-isobutylphenyl)propionic acid] was selected as nonlimiting example.

500 μl of a 10 mg/ml C16 protein-comprising potassium phosphate solution (5 mM, pH 8.0) were mixed with 100 μl of an ibuprofen solution (5 mg/ml in isopropanol). The C16 protein microbead formation was induced by adding 1 ml of 1 M potassium phosphate buffer (pH 8.0). The batch was incubated for 1 h at room temperature and then centrifuged for 10 min at 20000×g. The pellet was washed twice with 5 ml of double-distilled $H_2O$.

Following precipitation with potassium phosphate, microbeads formed in the batch with C16 protein and ibuprofen. These were comparable in morphological terms with those of a standard batch with C16 protein but without active substance. The packing of ibuprofen into the C16 protein microbeads was carried out quantitatively in this batch, and this was the reason why no ibuprofen could be detected by means of absorption photometry in the supernatant following induction of the microbead formation. As a result of an a specific proteolytic degradation of the ibuprofen-laden C16 microbeads with proteinase K (2.25 U) in 1 ml of 5 mM potassium phosphate buffer pH 8, the active substance could be released.

A proteolytic digestion of the ibuprofen-laden C16 protein microbeads in a pepsin-comprising batch (analogous to example 2) did not lead to the release of the active substance. The treatment of the ibuprofen-laden C16 protein microbeads in pancreatin-comprising batches (analogous to example 2) led to the release of the active substance. Accordingly, the C16 microbeads can provide protection against stomach protease and the very acidic pH values that prevail in the stomach. However, release under intestinal conditions is possible. C16 Microbeads are therefore suitable, inter alia, for the packing and formulation of perorally administered active substances which are absorbed or effective in the intestine and which should be protected upon passing through the stomach.

The invention claimed is:

1. A cosmetic preparation comprising a water-insoluble or a poorly water-soluble effect substance formulated with an amphiphilic self-assembling spider silk C16 protein having the amino acid sequence of SEQ ID NO: 1 and a cosmetic auxiliary.

2. A pharmaceutical preparation comprising a water-insoluble or a poorly water-soluble effect substance formulated with an amphiphilic self-assembling spider silk C16 protein having the amino acid sequence of SEQ ID NO: 1 and a pharmaceutical auxiliary.

3. An agrochemical preparation comprising a water-insoluble or a poorly water-soluble effect substance formulated with an amphiphilic self-assembling spider silk C16 protein having the amino acid sequence of SEQ ID NO: 1 and an agrochemical auxiliary.

* * * * *